(12) United States Patent
Vaillancourt

(10) Patent No.: US 7,037,302 B2
(45) Date of Patent: May 2, 2006

(54) POSITIVE FLOW NEEDLELESS CONNECTOR

(76) Inventor: Vincent L. Vaillancourt, deceased, late of Livingston, NJ (US); by Patricia B. Vaillancourt, legal representative, 14 Bunyan Dr., Livingston, NJ (US) 07039

( * ) Notice: Subject to any disclaimer, the term of this patent is extended or adjusted under 35 U.S.C. 154(b) by 710 days.

(21) Appl. No.: 10/236,141

(22) Filed: Sep. 6, 2002

(65) Prior Publication Data

US 2003/0120221 A1     Jun. 26, 2003

Related U.S. Application Data

(60) Provisional application No. 60/317,462, filed on Sep. 7, 2001.

(51) Int. Cl.
  A61M 25/16    (2006.01)
  A61M 25/18    (2006.01)
  A61M 39/00    (2006.01)
  A61M 39/10    (2006.01)

(52) U.S. Cl. ...................... 604/533; 604/905

(58) Field of Classification Search ............ 604/93.01, 604/246–249, 256, 523, 533–535, 537–538, 604/905; 251/149, 149.1, 149.4, 149.6
See application file for complete search history.

(56) References Cited

U.S. PATENT DOCUMENTS

| | | | | |
|---|---|---|---|---|
| 5,242,432 A | * | 9/1993 | DeFrank | 604/284 |
| 5,360,408 A | * | 11/1994 | Vaillancourt | 604/198 |
| 5,380,306 A | * | 1/1995 | Brinon | 604/244 |
| 5,439,451 A | * | 8/1995 | Collinson et al. | 604/247 |
| 5,470,319 A | * | 11/1995 | Mayer | 604/167.02 |
| 5,509,912 A | * | 4/1996 | Vaillancourt et al. | 604/537 |
| 5,520,665 A | * | 5/1996 | Fleetwood | 604/537 |
| 5,520,666 A | * | 5/1996 | Choudhury et al. | 604/537 |
| 5,549,577 A | * | 8/1996 | Siegel et al. | 604/256 |
| 5,694,686 A | * | 12/1997 | Lopez | 29/890.126 |
| 6,050,978 A | * | 4/2000 | Orr et al. | 604/249 |
| 6,063,062 A | * | 5/2000 | Paradis | 604/249 |
| 6,113,068 A | * | 9/2000 | Ryan | 251/149.4 |
| 6,299,131 B1 | * | 10/2001 | Ryan | 251/149.1 |

* cited by examiner

*Primary Examiner*—Loan H. Thanh
(74) *Attorney, Agent, or Firm*—Francis C. Hand; Carella, Byrne, Bain etal.

(57) ABSTRACT

The positive flow needleless connector has a cannula slideably mounted within a tubular housing. A sleeve-like septum seals the cannula from an outside environment while also sealing an internal chamber of the cannula from a flow path in a male luer housing. Movement of the cannula from an extended position to a retracted position against the force of a spring exposes a second inlet of the cannula to the flow path of the male luer housing to permit flow therebetween. During disconnect, the inlet from the cannula is sealed prior to the cannula returning the extended position. This allows fluid to move from a reservoir between the cannula and septum to move into the passage of the male luer housing.

15 Claims, 2 Drawing Sheets

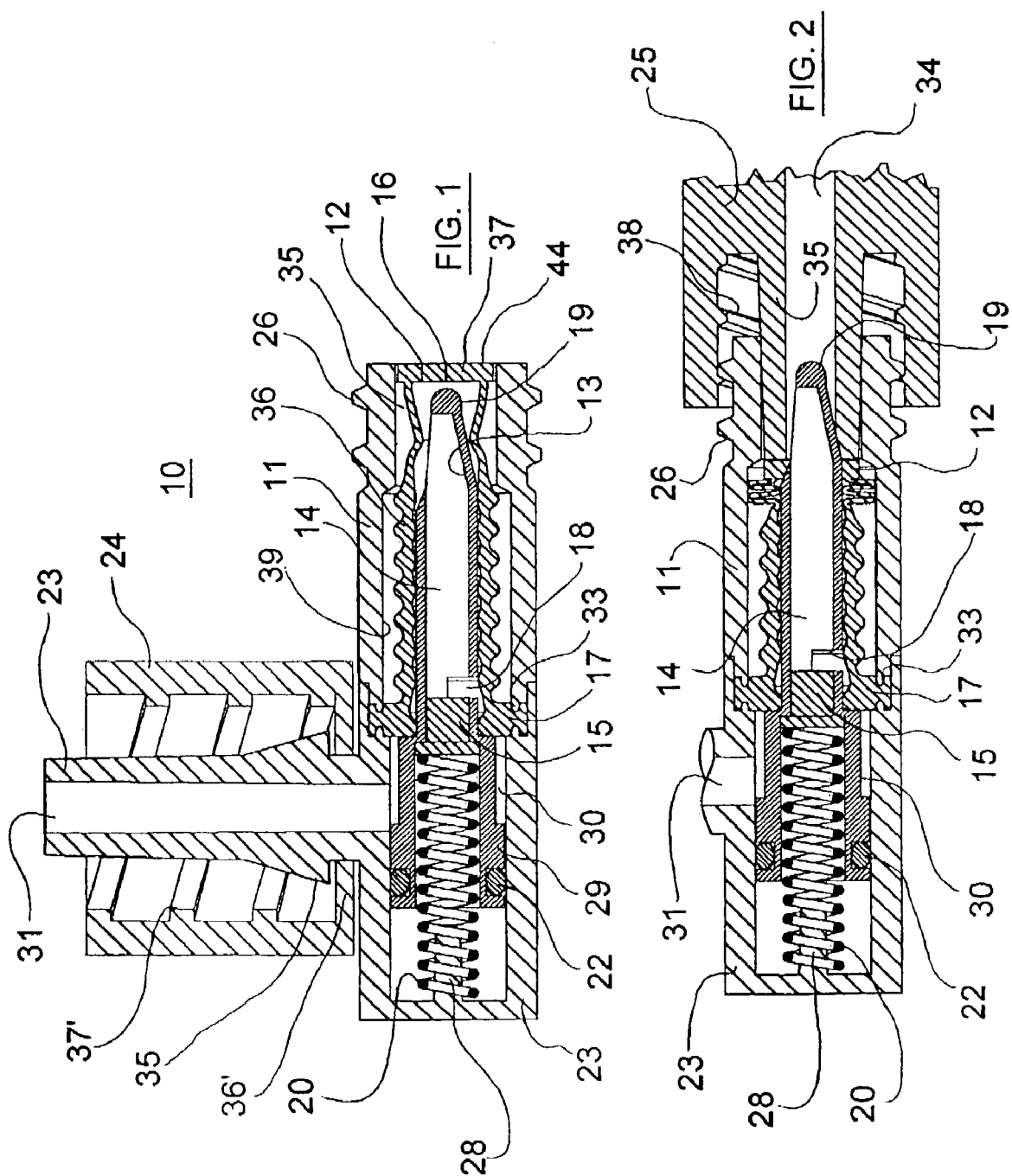

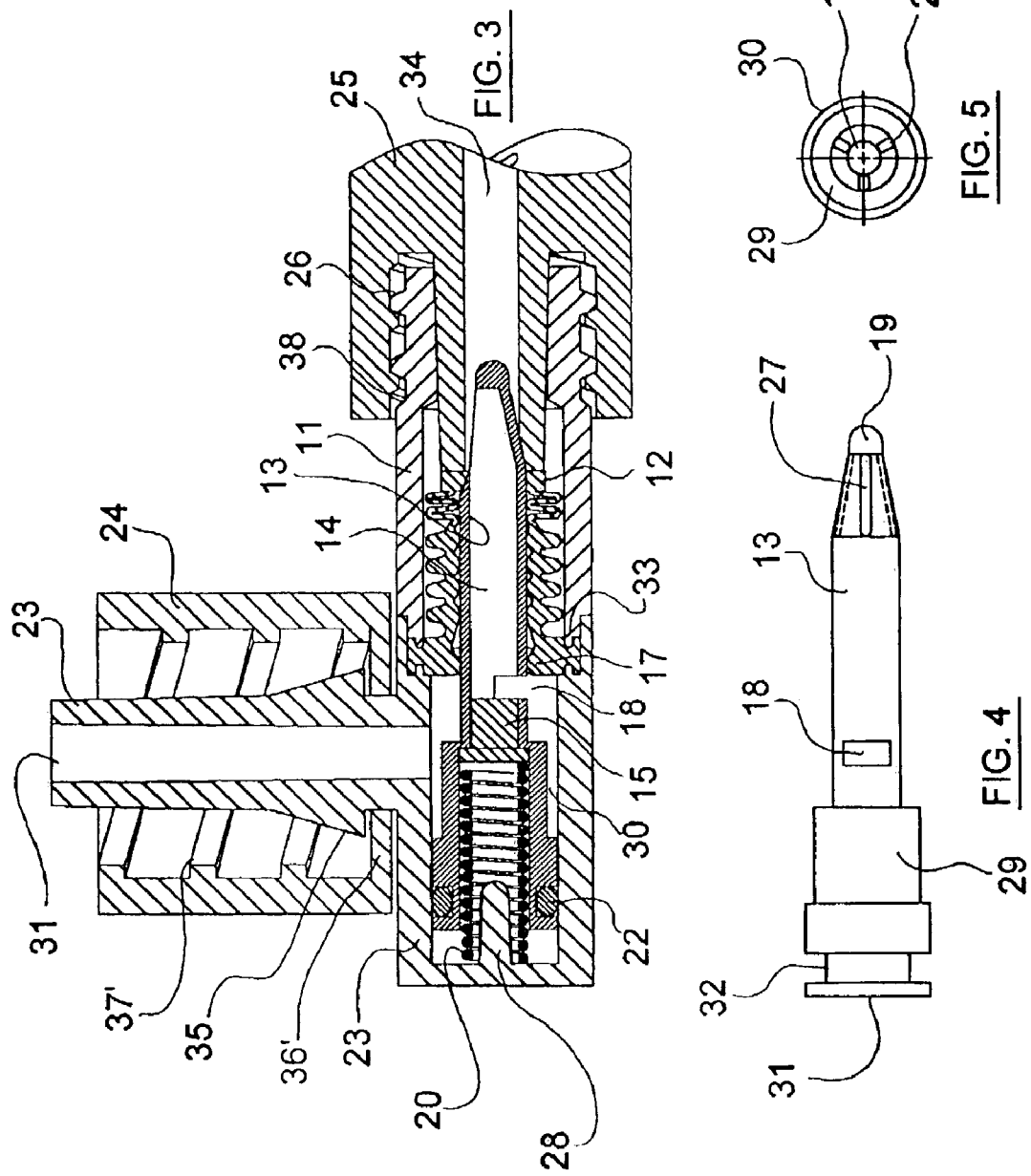

POSITIVE FLOW NEEDLELESS CONNECTOR

This is application claims priority of a Provisional Patent Application Ser. No. 60/317,462, filed Sep. 7, 2001.

This invention relates to a positive flow needleless connector. More particularly, this invention relates to positive flow needleless connector for use in the health care industry.

Heretofore, various types of connector assemblies have been known for connecting various types of medical components together. In some cases, the connector assemblies have been constructed to effect a rapid connection and disconnection between two lines for conveying fluids to a patient. In other cases, connector assemblies have been constructed to maintain a needle in a sterile connector, for example, where a syringe or a like structure is to be connected to a catheter or the like for the infusion of fluids into a patient or for removal of blood from a patient. Still, in other cases, connector assemblies have been constructed to protect against a needle stick from a needle employed in a medical component or instrument, which is to be connected to another medical component.

In particular, to overcome the use of needles for medicament transfer various needleless connectors have been devised. Generally, these devices have a septum which may be swabable to disinfect the septum face prior to engagement with a prefilled syringe or the like which has "just" been removed from a sterile package. After use, the syringe is discarded or another syringe with physiological saline is used to clear the line of any residual medicament. In many cases, upon removal of the syringe, there is retrograde flow of blood from the blood vessel back into the connector. Over a short period of time, this blood may clot and cause line impatentcy.

Various methods have been forwarded to overcome this concern. U.S. Pat. No. 5,616,130 describes a needleless connector having positive flow upon disconnect. As described, the opening and closing of a membrane of the connector depends upon a leaf spring which subjects a slit of the membrane to expansive forces upon retraction. A rubber member collapses during insertion and returns to a normal state after uncoupling thereby reducing the internal volume of the connector. Amongst other concerns, this structure requires a significant insertion force to affect coupling.

Another method is described in U.S. Pat. No. 5,439,451 in which the working structure is encased in an elastomeric sheath. Amongst other concerns, this structure is bulky and retains a significant reservoir of medicament during infusion.

Briefly, the invention provides a positive flow needleless connector in the form of a closed system female connector which can readily be swabbed to disinfect a contact surface immediately on site prior to forming a connection with a conventional male luer adaptor. Upon disconnect, there is a residual flow of infused fluid downstream, for example, into a tubing assembly.

The female connector comprises a housing adapted to receive a male luer adaptor. A hollow cannula is contained within the housing over which an elastomeric membrane is placed. The cannula is sealed from a second chamber by a portion of the membrane sidewall. A spring is aligned with the cannula to allow for axial movement of the cannula.

Upon insertion of a male luer adaptor into the female housing, the membrane is opened and slides up over the cannula. Upon further movement of the luer adaptor into the housing, the spring collapses with attendant axial movement of the cannula. The second chamber is opened to allow fluid flow. The second chamber has an opening for fluid egress into a luer connector lumen (normally a male luer adaptor), which may be connected to a tubing line.

Upon disconnect, the spring axially returns the cannula to the forward position thereby closing off the seal between the two chambers. Upon total disconnection, the membrane recovers and closes off the front portion of the cannula thereby sealing off the fluid path from the environment. After the second chamber is sealed off from the first chamber, there continues to be movement of the cannula due to the spring. This movement reduces the size of the second chamber forcing fluid out into the male luer adaptor.

In this manner, a needleless connection is achieved with a pre-wiped membrane (sterile surface). When the two portions of the coupling are decoupled there is a residual flow of infused fluid, which prevents blood from entering the line and potentially causing loss of patentcy.

These and other objects and advantages of the invention will become more apparent from the following detailed description taken in conjunction with the accompanying drawings wherein:

FIG. 1 illustrates a cross sectional view of a female connector constructed in accordance with the invention;

FIG. 2 illustrates in a cross sectional view of the female connector of FIG. 1 with a male luer adaptor partially coupled showing the membrane of the female connector moved over the cannula;

FIG. 3 illustrates a cross sectional view of the female connector of FIG. 1 with the male luer adaptor totally coupled as would be used by a practitioner;

FIG. 4 illustrates a view of the cannula used in the female connector; and

FIG. 5 illustrates an end view of the cannula as seen from the location of the membrane.

DETAILED DESCRIPTION OF THE PREFERRED EMBODIMENT

Referring to FIG. 1, the positive flow needleless connector 10 is in the form of a female connector having a tubular housing 11 and a male luer housing 23 secured to the tubular housing 11 and defining a flow path 31. The two housings 11, 23 are joined together, for example, using ultrasonics. Other the methods of sealing may also be employed, such as adhesives and heat.

As illustrated, the male luer housing 23 has a tubular portion receiving the tubular housing 10 in coaxial relation and a stem portion that extends perpendicularly of the tubular portion and the housing 11 to define a flow path 31 for connection to a tubing line (not shown).

The connector 10 has an elastomeric membrane or septum 12 mounted within the tubular housing 11. As illustrated, the septum 12 has a tubular portion concentrically within the tubular housing 11 formed of a forward non-corrugated segment 35 and a corrugated segment 36. In addition, the septum 12 has a body portion 37 of flat disk-shape closing the tubular portion 35, 36. This body portion has a flat swabable face 44 and a centrally located slit 16 or zone of weakening. The septum 12 also has an outwardly directed flange 17 at an opposite end of the corrugated segment 36 that is disposed in sealed in relation between and to the tubular housing 11 and the tubular portion of the male luer housing 23. To this end, an annular groove is formed in each of the housings 11, 23 to receive the circumferencial periphery 33 of the flange 17 therein in a seal-tight manner.

The connector 10 also has a cannula 13 slidably mounted concentrically within the tubular housing 11 for movement between an extended position as shown in FIG. 1 and a retracted position as shown in FIG. 3

Referring to FIGS. 1 and 4, the cannula 13 is hollow and has an internal chamber or lumen 14, three circumferentially disposed inlets 27 in the form of elongated slots (see FIG. 5) at one end which communicates with the chamber 14 and an outlet 18 spaced from the inlets 27 and communicating with the chamber 14 at an opposite end.

As shown in FIG. 1, the septum 12 is mounted over the cannula 13 so that the corrugated segment 36 fits over the cannula 13 to seal over the outlet 18 when the cannula 13 is in the extended position shown. The forward inlet 27 is formed within a tapered portion of the cannula 13 and is spaced from the non-corrugated segment 35 of the septum 12.

The forward end 19 of the cannula 13 is tapered for purposes as explained below and has a blunt tip that is disposed opposite the slit 16 in the septum 12 for purposes as described below.

The cannula 13 includes an annular shoulder 29 that abuts the flange 17 of the septum 12 in the extended position of the cannula 13. In addition, a seal ring 22 is disposed in a groove of the cannula 13 to seal against the tubular portion of the male luer housing 23. As illustrated, this annular shoulder 29 is spaced from the tubular portion of the male luer housing 23 to define a reservoir 30 therewith that is in communication with the flow path 31 for purposes described below.

The connector 10 also has a spring 20 mounted in the tubular portion of the male luer housing 23 on a fixed stem 28 in order to bias the cannula 13 from the retracted position of FIG. 3 into the extended position of FIG. 1. The spring 20 abuts against a plug 15 that is, in turn, abutted against an internal shoulder of the cannula 13. This plug 15 also serves to close off the internal chamber 14 of the cannula from the spring 20.

As shown in FIG. 1, the tubular housing 11 has an external thread 26 and the male luer housing 23 carries a locking ring 24 with an internal thread 37'. As indicated, the locking ring 24 has an internal flange 36' that abuts against a tapered shoulder 35 of the male luer housing 23 in order to be retained in place in a freely rotatable manner.

In order to assemble the connector 10, the plug 15 is fitted into the cannula 13 to seal off the chamber 14, the spring 20 is disposed in the cannula 13 in abutment with the plug 15 and the seal ring 22 is put into place. The cannula 13 and spring 20 are then slid into the tubular portion of the male luer housing 23.

Next, the septum 12 is slid over the cannula 13 until the flange 17 abuts the annular lip of the tubular portion of the male luer housing 23 and is seated against the annular shoulder 29 of the cannula.

The tubular housing 11 is then pressed into place so as to compress the periphery of the flange 17 to effect a seal-tight fit. The tubular housing 11 is then secured to the male luer housing 23 in a manner as described above. Note is made that the assembly of the connector 10 may be performed in other manners than as above.

As shown in FIG. 1, the disk-like body 37 of the septum 12 is sealingly disposed within the internal wall of the tubular housing 11. In addition, the tubular housing 11 has an internal recess 39 of larger inside diameter than the interior wall of the forward end of the tubular housing 11 to accommodate resilient collapsing of the segments 35, 36 of the septum 12 as described below.

When the septum 12 is in place, the corrugated segment 36 covers over the outlet 18 of the cannula 13. Thus, the chamber 14 of the cannula 13 is sealed off from the reservoir 30 that is in communication with the flow path 31 in the male luer housing 23.

Referring to FIG. 2, wherein like reference characters indicate like parts as above, opening and closing of the female connector 10 is performed using a male adaptor 25. As illustrated, the male adaptor 25 is in the form of a male luer adaptor having a central passage 34 for a flow of fluid and a hollow projecting nose 35. In addition, the adaptor 25 has a locking ring integral therewith with an internal thread 38 for engaging corresponding threads 26 on the female connector 10.

As illustrated, the outer diameter of the nose of the adaptor 25 is smaller than the inner diameter of the forward end of the tubular housing 11 in order to penetrate the housing 11. In addition, the inner diameter of the nose is larger than the diameter of the blunt tip 19 of the cannula but smaller than the untapered part of the cannula 13 in order to come into contact with the cannula at an intermediate point.

In order to form a connection in the field, the face of the septum 12 is swabbed on site. Next, the nose of the male adaptor 25 is then abutted against the flat disk-like body 37 of the septum 12. The adaptor 25 is then pushed forwardly so that the blunt tip 19 of the cannula 13 passes through the slit 16 of the septum 12. Continued motion of the nose pushes the body 37 of the septum 12 along the tapered surface of the cannula 13 and into the recess 39 of the tubular housing 11 so that the non-corrugated segment 35 collapses into a bellows-like shape as shown in FIG. 2. In this respect, the enlarged recess 39 accommodates the diametric expansion of the non-corrugated segment 35.

At this time, the nose of the adaptor 25 abuts against the tapered surface of the forward end of the cannula 13 as indicated in FIG. 2 and the adaptor 25 can be rotated to thread onto the housing 11. During this time, the inlet 27 of the cannula 13 is exposed so that fluid may flow from the passage 34 of the adaptor 25 into the chamber 14 of the cannula 13.

After the nose of the adaptor 25 abuts against the cannula 13, rotation of the adaptor 25 on the threads 26 of the housing 11 causes the nose to now push the cannula 13 against the bias of the spring 20 into the retracted position shown in FIG. 3. During this time, the nose now deforms the corrugated segment 36 of the septum 12 within the enlarged recess 39 of the tubular housing 11. At the same time, the outlet 18 of the cannula 13 moves past the flange 17 of the septum 12 into alignment with the reservoir 30 so that communication is now made between the passage of the adaptor 25 and the flow path 31 of the male luer housing 23 via the cannula chamber 14 and reservoir 30.

In order to conduct a disconnect or uncoupling, the male adaptor 25 is unthreaded from the tubular housing 11. Initially, the spring 20 causes the cannula 13 to move from the retracted position shown in FIG. 3 towards the intermediate position shown in FIG. 2. During this time, the outlet 18 of the cannula 13 is moved past the flange 17 and into sealing contact with the corrugated segment 36 of the septum 12 thereby sealing off the chamber 14 of the cannula 13 from the reservoir 30. Continued movement of the cannula 13 under the force of the spring 20 causes the fluid in the reservoir 30 to pass into the flow path 31 of the male luer housing 23 until the annular shoulder 29 of the cannula 13 abuts against the flange 17 of the septum 12. This residual flow of infused fluid prevents blood from entering the tubing line and connector 10 that might otherwise cause a loss of patentcy.

Continued retraction of the male adaptor 25 from the intermediate position of FIG. 2 to the position of FIG. 1 allows the non-corrugated segment 35 of the septum 12 to return to the unstressed state illustrated in FIG. 1 while the disk-like body 37 closes to seal off the cannula 13 from the outside environment.

The invention thus provides a positive flow needleless connector that is constructed to prevent a retrograde flow of blood from a blood vessel back into the connector during an uncoupling procedure.

The invention further provides a positive flow needleless connector which can be constructed in a relatively simple manner and which is relatively easy to use.

What is claimed is:

1. A female connector comprising
   a tubular housing;
   a male luer housing mounted on said tubular housing and defining a flow path;
   an elastomeric septum having a tubular portion concentrically within said tubular housing, a body portion at one end of said tubular portion closing said tubular portion and an outwardly directed flange at an opposite end of said tubular portion disposed in sealed relation to said tubular housing;
   a cannula slideably mounted concentrically within said tubular housing for movement between an extended position and a retracted position, said cannula having a chamber therein concentrically within said tubular portion of said septum, at least one inlet at one end communicating with said chamber and an outlet spaced from said inlet and communicating with said chamber, said outlet being disposed in sealed relation with said tubular portion of said septum in said extended position of said cannula and being disposed in communication with said flow path of said male luer housing in said retracted position of said cannula; and
   a spring biasing said cannula into said extended position.

2. The female connector as set forth in claim 1 wherein said cannula has a blunt tip facing said body portion of said septum and said body portion has a slit for passage of said blunt tip therethrough in response to collapsing of said tubular portion to expose said inlet to a fluid flow into said passage of said cannula.

3. The female connector as set forth in claim 1 wherein said cannula has an annular shoulder abutting said flange of said septum to seal said flow path in said male luer housing from said outlet of said cannula in said extended position of said cannula.

4. The female connector as set forth in claim 3 wherein said annular shoulder is spaced from said tubular portion of said male luer housing to define a reservoir therewith whereby upon movement of said cannula from a retracted position towards said extended position and sealing of said tubular portion of said septum over said outlet in said cannula, fluid in said reservoir is expelled into said flow path in said male luer housing.

5. The female connector as set forth in claim 1 wherein said cannula is hollow.

6. The female connector as set forth in claim 5 wherein said cannula has an internal shoulder and which further comprises a plug abutted against said shoulder to seal said chamber in said cannula at one end and abutted against said spring.

7. The female connector as set forth in claim 1 wherein said cannula has a tapered end having said inlet therein and said tubular portion of said septum includes a collapsible non-corrugated segment extending from said body and spaced concentrically from said tapered end cannula and a corrugated segment slideably mounted on said cannula.

8. The female connector as set forth in claim 7 wherein said tubular housing has a recess concentric to said corrugated segment.

9. The female connector as set forth in claim 1 wherein said male luer housing has a tubular portion secured to said tubular housing and a stem portion perpendicular to said tubular portion and having said flow path therein.

10. In combination,
    a tubular housing;
    a male luer housing mounted on said tubular housing and defining a flow path;
    a septum having a tubular portion concentrically within said tubular housing, a body portion at one end of said tubular portion closing said tubular portion and an outwardly directed flange at an opposite end of said tubular portion disposed in sealed relation to said tubular housing;
    a cannula slideably mounted concentrically within said tubular housing for movement between an extended position and a retracted position, said cannula having a chamber therein concentrically within said tubular portion of said septum, an inlet at one end communicating with said chamber and an outlet spaced from said inlet and communicating with said chamber, said outlet being disposed in sealed relation with said tubular portion of said septum in said extended position of said cannula and being disposed in communication with said flow path of said male luer housing in said retracted position of said cannula;
    a spring biasing said cannula into said extended position; and
    a male adaptor having a central passage for a flow of fluid and a hollow projecting nose for pushing said body of said septum over said cannula to resiliently collapse said tubular portion of said septum and to expose said inlet in said cannula to said central passage.

11. The combination as set forth in claim 10 wherein said cannula has a tapered forward end for fitting into said nose of said male adaptor and a main portion of an outside diameter greater than an internal diameter of said nose.

12. The combination as set forth in claim 10 wherein said cannula has a blunt tip facing said body portion of said septum and said body portion has a slit for passage of said blunt tip therethrough in response to said nose of said adaptor collapsing said tubular portion to expose said inlet to a fluid flow from said passage of said adaptor into said passage of said cannula.

13. The combination as set forth in claim 10 wherein said cannula has an annular shoulder abutting said flange of said septum to seal said flow path in said male luer housing from said outlet of said cannula in said extended position of said cannula.

14. The combination as set forth in claim 13 wherein said annular shoulder is spaced from said tubular housing to define a reservoir therewith whereby upon movement of said cannula from said retracted position to said extended position and sealing of said tubular portion of said septum over said outlet in said cannula fluid in said reservoir is expelled into said flow path in said male luer housing.

15. The combination as set forth in claim 10 wherein said tubular portion of said septum includes a collapsible non-corrugated segment adjacent said body and spaced from said cannula and a corrugated segment slideably mounted on said cannula.

* * * * *